(12) United States Patent
Kim et al.

(10) Patent No.: US 11,878,190 B2
(45) Date of Patent: Jan. 23, 2024

(54) TRIBOELECTRIC GENERATOR INCLUDING NANO-COMPOSITE TIME-LIMITED VIA SELECTIVE ULTRASOUND APPLICATION THERETO AND NEUROSTIMULATION THERAPY DEVICE USING THE SAME

(71) Applicant: ENERGY MINING CO., LTD., Suwon-si (KR)

(72) Inventors: SangWoo Kim, Yongin-si (KR); Min Ki Kang, Suwon-si (KR); Bo Sung Kim, Suwon-si (KR); Joon Ha Hwang, Suwon-si (KR); So Hee Kim, Hwaseong-si (KR); Young Jun Kim, Daejeon (KR); Dong Min Lee, Daejeon (KR); Jae Hwan Jung, Daejeon (KR); Hyoung Taek Kim, Suwon-si (KR); Dong Hyeon Kang, Suwon-si (KR); Ji Hyun Park, Anseong-si (KR)

(73) Assignee: ENERGY MINING CO., LTD, Suwon-si (KR)

( * ) Notice: Subject to any disclaimer, the term of this patent is extended or adjusted under 35 U.S.C. 154(b) by 212 days.

(21) Appl. No.: 17/515,675

(22) Filed: Nov. 1, 2021

(65) Prior Publication Data
US 2022/0134135 A1    May 5, 2022

(30) Foreign Application Priority Data

Nov. 3, 2020 (KR) .................. 10-2020-0145170

(51) Int. Cl.
*A61N 7/00*    (2006.01)
*C08L 101/16*    (2006.01)
(Continued)

(52) U.S. Cl.
CPC .............. *A61N 7/00* (2013.01); *C08L 101/16* (2013.01); *A61N 2007/0026* (2013.01);
(Continued)

(58) Field of Classification Search
CPC .... A61N 7/00; A61N 2007/0026; A61N 7/02; C08L 101/16; C08L 2201/06; C08L 2203/02; B82Y 5/00; B82Y 30/00
See application file for complete search history.

(56) References Cited

U.S. PATENT DOCUMENTS

| 2002/0055731 | A1* | 5/2002 | Atala | ................. A61K 41/0047 604/20 |
| 2002/0107470 | A1* | 8/2002 | Richards | .............. A61K 9/0097 604/20 |

(Continued)

FOREIGN PATENT DOCUMENTS

KR    10-2011-0138917 A    12/2011

OTHER PUBLICATIONS

Yue Shi et al., "Recent Development of Implantable and Flexible Nerve Electrodes", Smart Materials in Medicine, vol. 1 (17 pages in English).

*Primary Examiner* — Hien N Nguyen
(74) *Attorney, Agent, or Firm* — NSIP Law

(57) ABSTRACT

Disclosure are a triboelectric generator including a nano-composite life-limited via selective ultrasound application thereto, and a neurostimulation therapy device using the same. Disclosure are a life-limited nano-composite that initiates biodegradation thereof upon application of focused ultrasound thereto, and to a neurostimulation therapy device for peripheral neuropathy treatment using an ultrasound-driven triboelectric generator based on the life-limited nano-composite. The device has a power source that is harmless to a human body and performs nerve stimulation treatment using this power source, and then causes biodegradation at a desired timing after the treatment is completed.

9 Claims, 3 Drawing Sheets

(51) Int. Cl.
  *B82Y 30/00*    (2011.01)
  *B82Y 5/00*     (2011.01)
(52) U.S. Cl.
  CPC ............... *B82Y 5/00* (2013.01); *B82Y 30/00* (2013.01); *C08L 2201/06* (2013.01); *C08L 2203/02* (2013.01)

(56) References Cited

U.S. PATENT DOCUMENTS

| | | | |
|---|---|---|---|
| 2006/0240078 A1* | 10/2006 | Jenkins | A23K 50/10 424/490 |
| 2010/0028453 A1* | 2/2010 | Yoo | C08J 3/12 424/178.1 |
| 2018/0021485 A1* | 1/2018 | Nishikawa | A61K 9/70 424/426 |
| 2019/0374638 A1* | 12/2019 | Bernstein | A61K 39/3955 |

* cited by examiner

TRIBOELECTRIC GENERATOR INCLUDING NANO-COMPOSITE TIME-LIMITED VIA SELECTIVE ULTRASOUND APPLICATION THERETO AND NEUROSTIMULATION THERAPY DEVICE USING THE SAME

BACKGROUND

Field

The present disclosure relates to a triboelectric generator including a nano-composite life-limited via selective ultrasound application thereto and a neurostimulation therapy device using the same.

The present disclosure relates to a life-limited nano-composite that initiates biodegradation thereof upon application of focused ultrasound thereto, and to a neurostimulation therapy device for peripheral neuropathy treatment using an ultrasound-driven triboelectric generator based on the life-limited nano-composite.

Description of Related Art

Peripheral neuropathy is a disease caused by damage or functional abnormality of the nervous system. Peripheral neuropathy is intractable, and has chronic and long-lasting characteristics. Thus, patients suffering from the peripheral neuropathy may experience significant deterioration in quality of life, sleep disturbance, and complications such as depression. For treatment of the peripheral neuropathy, neurostimulation therapy which electrically stimulates nerves is applied. Demand of the neurostimulation therapy increases with increase in the aging population. Thus, development of an implantable medical device capable of permanent treatment of the peripheral neuropathy is actively being carried out.

Recently, a medical device using a life-limited material that is dissolved and absorbed in a body after a function thereof has been completed has been developed. The device uses electromagnetic induction energy transmission techniques such as RFID and NFC as a power source. However, harmlessness of NFC to the human body has not been verified. When using RFID transmission technique, the device may not be miniaturized because RFID requires a complex circuit. Further, due to a short penetration depth smaller than 1 cm, an inserted site thereof is mostly limited to a subcutaneous layer, so that a long lead wire is required to connect from the energy source to a deep part in the body. The difficulty in miniaturization and the limited inserted position may disallow minimizing a risk to the human body.

A conventional life-limited material relies on passive control based on the material's biodegradation characteristics and thickness control thereof. Thus, there is no means to control biodegradation after insertion of a medical device into the body. It is difficult to control a lifespan of the material due to a random mass loss of the material. If the material melts before termination of treatment, the device does not function and treatment is not complete. When the material does not dissolve for a long time after the completion of the treatment, reoperation may be required, or serious pathological problems such as inflammation and complications may occur in the body.

According to the limitations of the conventional technique as described, it is urgent to develop a new concept material/device technique that has a battery-free power source that may be harmless to the human body and may accurately biodegrade at a desired timing after treatment of peripheral neuropathy is finished.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

One purpose of the present disclosure is to provide a methodology that may overcome the limitations of the conventional techniques by proposing a neurostimulation material/device technique for peripheral neuropathy treatment based on an ultrasound-driven triboelectric energy generation technique and a life-limited nanocomposite.

One purpose of the present disclosure is to provide a device which is able to treat peripheral neuropathy, in which miniaturization of the device is possible and there is no limitation on an inserted position thereof in the body, and harm thereof to the human body is minimized, and current generated via ultrasound application thereto directly stimulates a nerve.

In addition, one purpose of the present disclosure is to provide a new concept of a life-limited nano-composite in which biodegradation of the composite may be controlled in vitro at a desired precise timing.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

One aspect of the present disclosure provides a nano-composite time-limited via selective ultrasound application thereto, the nano-composite comprising: a life-limited matrix; and a nano-carrier embedded or contained in the matrix, wherein the nano-carrier is decomposed when a focused ultrasound is applied thereto, wherein when the focused ultrasound is applied to the nano-composite, the nano-carrier is decomposed and, thus, the matrix becomes porous, thereby increasing a biodegradation rate of the matrix.

In one implementation of the nano-composite, the matrix is made of a biodegradable resin.

In one implementation of the nano-composite, the biodegradable resin includes at least one selected from a group consisting of PLGA (polylactic-co-glycolic acid), PLA (Polylactic Acid), PEG (Polyethylene glycol), PEO (polyethylene oxide), PBS (Phosphate Buffered Saline), PCL (poly ε-caprolactone), PEEK (Polyetheretherketone), PTHPMA (poly(tetrahydropyranyl-2-methyl methacrylate)), and PPG (Polypropylene Glycol).

In one implementation of the nano-composite, the nano-carrier includes at least one selected from a group consisting of polymersome, MOF (metal-organic framework), exosome, liposome, ectosome, and nanoparticles.

In one implementation of the nano-composite, the polymersome includes a block copolymer composed of a life-limited polymer block.

In one implementation of the nano-composite, the MOF includes a biocompatible ultrasound responsive MOF.

In one implementation of the nano-composite, the nano-carrier further includes an enzyme, catalyst or drug for promoting the biodegradation rate of the matrix.

One aspect of the present disclosure provides a triboelectric generator including a nano-composite time-limited via selective ultrasound application thereto, the generator comprising: an electrode made of a biodegradable material; a membrane disposed to face toward the electrode and spaced apart from the electrode; and an encapsulation portion surrounding the electrode and the membrane, wherein each of the membrane and the encapsulation portion is made of a nano-composite time-limited via selective ultrasound application thereto, wherein the nano-composite includes: a life-limited matrix; and a nano-carrier embedded or contained in the matrix, wherein the nano-carrier is decomposed when a focused ultrasound is applied thereto, wherein when general ultrasound is applied to the nano-composite, the membrane vibrates such that triboelectricity is generated via friction between the membrane and the electrode, wherein when focused ultrasound is applied to the nano-composite, the nano-carrier is decomposed and, thus, the matrix becomes porous, thereby increasing a biodegradation rate of the matrix.

In one implementation of the generator, the matrix is made of a biodegradable resin.

In one implementation of the generator, the biodegradable resin includes at least one selected from a group consisting of PLGA (polylactic-co-glycolic acid), PLA (Polylactic Acid), PEG (Polyethylene glycol), PEO (polyethylene oxide), PBS (Phosphate Buffered Saline), PCL (poly ε-caprolactone), PEEK (Polyetheretherketone), PTHPMA (poly(tetrahydropyranyl-2-methyl methacrylate)), and PPG (Polypropylene Glycol).

In one implementation of the generator, the nano-carrier includes at least one selected from a group consisting of polymersome, MOF (metal-organic framework), exosome, liposome, ectosome, and nanoparticles.

In one implementation of the generator, the polymersome includes a block copolymer composed of a life-limited polymer block.

In one implementation of the generator, the MOF includes a biocompatible ultrasound responsive MOF.

In one implementation of the generator, the nano-carrier further includes an enzyme, catalyst or drug for promoting the biodegradation rate of the matrix.

In one implementation of the generator, a dielectric material is coated on a face of the electrode facing toward the membrane to increase the generation of triboelectricity.

In one implementation of the generator, the electrode, the membrane, and the encapsulation portion constitute one unit of the generator, wherein the generator includes a stack of a plurality of units.

One aspect of the present disclosure provides a neurostimulation therapy device comprising: the triboelectric generator as defined above; and a stimulation electrode connected to the triboelectric generator, wherein the stimulation electrode is connected to a stimulation target nerve and applies electrical current generated from the triboelectric generator to the nerve.

In one implementation of the device, the stimulating electrode is composed of a conductor pattern including one or more electrodes.

According to the present disclosure, the technique that may overcome the limitations of the conventional implantable medical device/neurostimulation device may be realized.

In addition to the effects as described above, specific effects in accordance with the present disclosure will be described together with following detailed descriptions for carrying out the disclosure.

DETAILED DESCRIPTIONS

Figure 1:
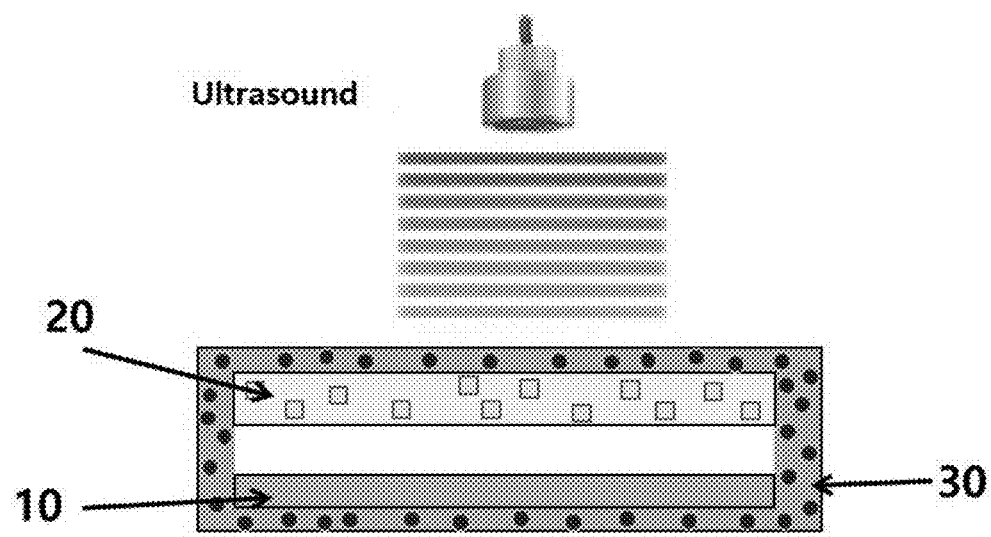
FIG. 1 shows the structure of an ultrasound-driven triboelectric generator according to an embodiment of the present disclosure.

For simplicity and clarity of illustration, elements in the figures are not necessarily drawn to scale. The same reference numbers in different figures represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure relates to a life-limited nano-composite in which biodegradation thereof is initiated when focused ultrasound is applied thereto. Further, the present disclosure relates to an ultrasound-driven triboelectric generator for peripheral neuropathy treatment including the life-limited nano-composite, and a nerve stimulation treatment technique using the same.

A nano-composite life-limited via selective ultrasound application thereto according to an embodiment of the present disclosure include a life-limited matrix; and a nano-carrier embedded or contained in the matrix, wherein the nano-carrier is decomposed when focused ultrasound is applied to the composite.

The life-limited nano-composite means a composite in which the nano-carrier decomposed via application of the focused ultrasound thereto is embedded or contained in the matrix. The nano-carrier may include polymersome, and a metal-organic framework (MOF), and may refer to a material that may insert or deliver other materials into molecules such that the other materials may be stored therein.

The life-limited matrix may be made of a biodegradable material, and the nano-carrier may be embedded or contained in the life-limited matrix. The biodegradable material used as the life-limited matrix may include PLGA (polylactic-co-glycolic acid), PLA (Polylactic Acid), PEG (Polyethylene glycol), PEO (polyethylene oxide), PBS (Phosphate Buffered Saline), PCL (poly ε-caprolactone), PEEK (polyetheretherketone), PTHPMA (poly(tetrahydropyranyl-2-methyl methacrylate)), PPG (Polypropylene Glycol), hydrogel, and collagen.

The nano-carrier may be decomposed via application of focused ultrasound thereto. That is, when the focused ultrasound is applied to the nano-carrier, mechanical stress generated by the application of the focused ultrasound is applied to a molecule to break weak bonds in the molecule. The nano-carrier may include polymersome or MOF (metal-organic framework).

Polymersome includes a block copolymer composed of a life-limited polymer block. When a block copolymer composed of monomer blocks with different polarities in the polymersome is exposed to a solvent having different polarities, inner and outer spaces of the polymersome are separated from each other via self-assembly, such that other molecules may be received in the inner space and may be stored or carried therein. The block copolymer constituting the polymersome may include a material made of a life-limited material block such as PLA-b-PEG and PCL-b-PEG. The block copolymer may include copolymers such as PLA-SS-PEG having SS-bonds or metal ligand bonds that are easily decomposed via application of the focused ultrasound thereto. When the focused ultrasound is applied to the polymersome, mechanical stress is applied to the polymer molecule to break the weak bonds in the polymer including the SS-bond and metal ligand bond as aforementioned, such that the polymersome is decomposed. The polymersome may include, for example, PEG-PLA, PEG-S-PLA, PEG-S-S-PLA, PEG-PPG, PEG-COO-SS-PPG, PEG-SS-PPG, PPG-[Cu]-PEG, PEG-b-PTHPMA, PEO-b-PI BMA, PEO-b-PMMA, etc.

MOF may include a biocompatible ultrasound responsive MOF. MOF is a crystalline material synthesized based on a combination of an organic ligand and a metal ion. Like the polymersome, MOF has the ability to contain and transport other materials therein. MOF may include various materials such as MIL and ZIF depending on a type and a binding manner of the organic ligand and the metal ion. When the focused ultrasound is applied to the MOF, mechanical stress is applied to the MOF and thus a metal-organic link bond is broken and thus the MOF is decomposed. MOF may include, for example, ZIF-90, ZIF-67, ZIF-8, ZIF-11, MIL-100(Cr), MIL-101(Cr), MIL-100(Fe), etc.

In another example, exosome, liposome, ectosome, or nanoparticles in addition to polymersome and MOF may be used as the nano-carrier.

In summary, the nano-composite life-limited via selective ultrasound application thereto according to an embodiment of the present disclosure may include the life-limited matrix; and the nano-carrier embedded or contained in the matrix, wherein the nano-carrier is decomposed via focused ultrasound application thereto. When genera ultrasound is applied thereto, the nano-carrier is not decomposed. However, when the focused ultrasound is applied thereto, the nano-carrier is decomposed such that the matrix becomes porous, thereby increasing biodegradability thereof. As the nano-carrier is decomposed via the application of focused ultrasound thereto, the matrix becomes porous and thus a contact area thereof with a body fluid expands, thereby increasing the biodegradation rate and decomposition thereof. In the life-limited nano-composite, both the matrix and the nano-carrier may have excellent biocompatibility.

In one example, enzymes and catalysts that decompose the matrix may be contained in the nano-carrier, and thus may further increase the biodegradation rate when the nano-carrier is decomposed. Available enzymes or catalysts include horseradish peroxidase, catalase, xanthine oxidase, phosphatases, esterases, protease, polyvinyl alcohol, pronase, Proteinase K, bromelain, lipase dehydrogenase, polyhydroxybutyrate, and the like.

The nano-composite life-limited via selective ultrasound application thereto according to an embodiment of the present disclosure has been described above. Hereinafter, a triboelectric generator including the nano-composite life-limited via selective ultrasound application thereto and a device for nerve stimulation treatment using the triboelectric generator will be described sequentially. Duplicate descriptions of the contents described above will be omitted.

FIG. 1 shows a structure of an ultrasound-driven triboelectric generator according to an embodiment of the present disclosure.

A triboelectric generator including the nano-composite time-limited via selective ultrasound application thereto according to an embodiment of the present disclosure includes an electrode 10; a membrane 20; and an encapsulation portion 30. The ultrasound-driven triboelectric generator is composed of the membrane, the electrode, and the encapsulation portion. As the membrane vibrates when ultrasound is applied thereto, the membrane and the electrode rub against each other to generate triboelectricity such that electrical current is generated by electrostatic induction.

The electrode 10 is made of a biodegradable material. The electrode may act as a friction material that generates triboelectricity when coming into contact with the membrane and at the same time, may act as a conductor that transmits the current to a neurostimulation electrode. The device for nerve stimulation treatment may include a separate stimulation electrode as described later from the electrode 10. The electrode 10 may include biodegradable magnesium, silicon, and PEDOT-PSS. The electrode 10 may be coated with a dielectric material to maximize triboelectricity generation. The dielectric material may include a biodegradable and life-limited polymer such as PLGA, PLA, PEG, PEO, PBS, PCL, PEEK, PTHPMA, PPG, or a combination thereof with MOF or polymersome.

As shown in FIG. 1, the membrane 20 faces toward the electrode 10 and is spaced apart from the electrode 10.

The membrane 20 generates triboelectricity while contacting and being removed from the electrode 10. The membrane may be made of a polymer material which has mechanical properties in which the membrane may vibrate well according to the application of ultrasonic waves thereto, and has an acoustic impedance similar to that of the human body. Alternatively, any material that is not electrically conductive may be used as the membrane. The membrane is made of preferably a material capable of generating a great triboelectricity when rubbing against a mating material.

The membrane may include the life-limited nano-composite as mentioned above. In this connection, the embedded nano-carrier is used to control the biodegradability and to control a surface potential, and a surface shape, and increase a dielectric constant to increase an output of the triboelectric generator.

The encapsulation portion 30 surrounds the electrode 10 and the membrane 20 as shown in FIG. 1, and serves to protect the electrode 10 and the membrane 20. A material of the encapsulation portion may include a material that protects the triboelectric generator from external human tissue. The life-limited nano-composite as mentioned above may be used as the material thereof.

The nano-composite time-limited via selective ultrasound application thereto include the life-limited matrix; and the nano-carrier embedded or contained in the matrix, wherein the nano-carrier is decomposed via the application of the focused ultrasound thereto. This composite has been described in detail above.

Figure 2:
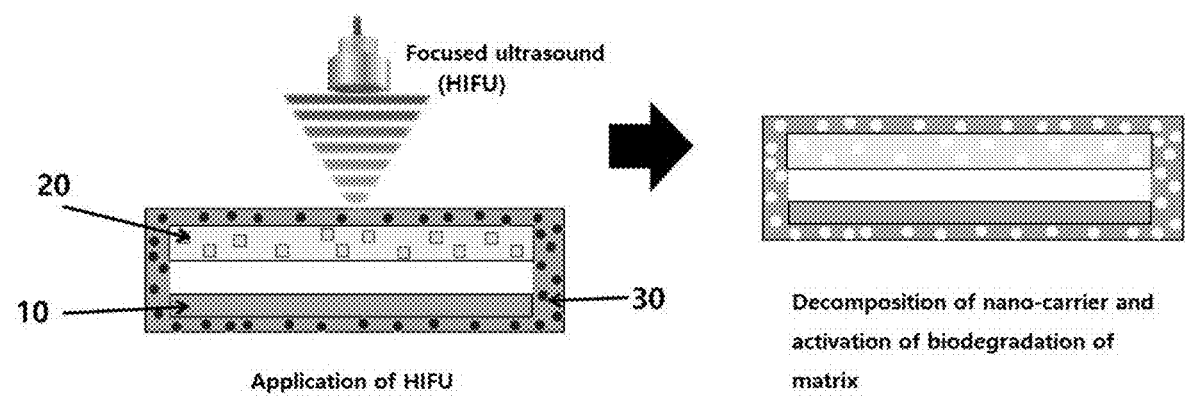
FIG. 2 shows a state in which biodegradation is activated when focused ultrasound is applied to a triboelectric generator including a life-limited nano-composite according to an embodiment of the present disclosure.

In the triboelectric generator including the nano-composite life-limited via selective ultrasound application thereto according to an embodiment of the present disclosure, electricity is generated via friction between the membrane and the electrode as the membrane vibrates when a general ultrasound is applied thereto. When the focused ultrasound is applied thereto, the nano-carrier is decomposed and thus, the matrix becomes porous, thereby increasing the biodegradation rate thereof. FIG. 2 shows a state in which biodegradation is activated when the focused ultrasound is applied to a triboelectric generator including a life-limited nano-composite according to an embodiment of the present disclosure.

In one example, an ultrasound-driven triboelectric generator according to an additional embodiment of the present disclosure may have a stacked structure in which a membrane and an electrode are repeatedly stacked based on a required output. That is, a unit may be composed of an electrode made of a biodegradable material; a membrane disposed to face toward the electrode and spaced apart from the electrode; and an encapsulation portion surrounding the electrode and the membrane. A plurality of units may be stacked vertically.

Figure 3:
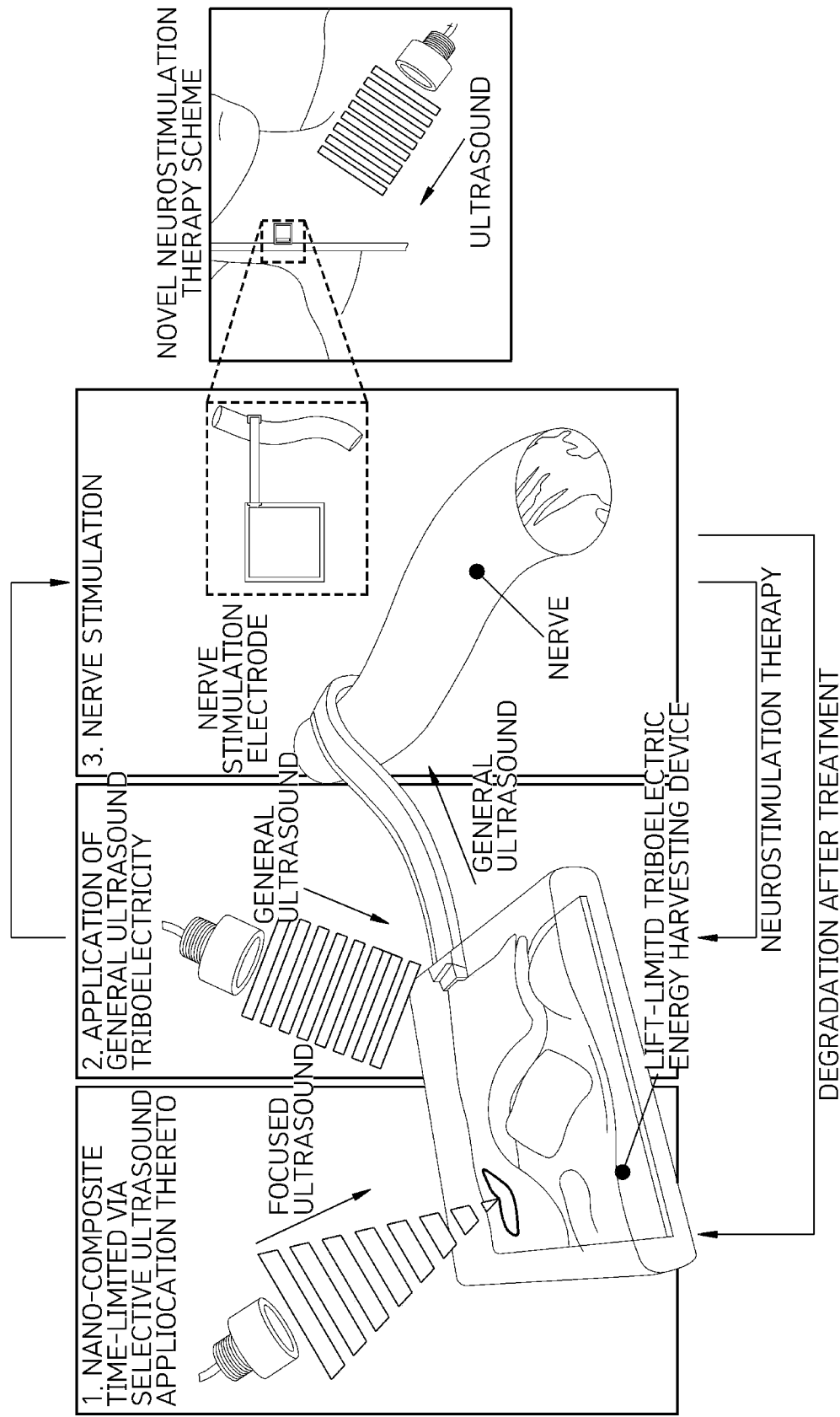
FIG. 3 shows a schematic diagram of an ultrasound-driven triboelectricity-based nerve stimulation technique using a life-limited nano-composite.

FIG. 3 shows a schematic diagram of an ultrasound-driven triboelectric nerve stimulation technique using a life-limited nano-composite. The triboelectric generator including the nano-composite life-limited via selective ultrasound application thereto according to an embodiment of the present disclosure may be used in the neurostimulation therapy device. In the ultrasound-driven triboelectric neurostimulation technique, when the general ultrasound is applied from a ultrasound source and is delivered to the neurostimulation device in the body, current may be generated due to electrostatic induction according to membrane vibration and triboelectric generation, and then the electric current may be applied to nerves via an electrode of the device, thereby electrically stimulating the nerves.

The ultrasound-driven triboelectric neurostimulation device is composed of the ultrasound-driven triboelectric generator that generates the current required for neurostimulation and a neurostimulation electrode that delivers the current to the nerve. Each of the generator and the neurostimulation electrode may include the life-limited material and the life-limited nano-composite.

The neurostimulation therapy device using the triboelectric generator including the nano-composite life-limited via selective ultrasound application thereto according to an embodiment of the present disclosure may include the triboelectric generator as described above including the nano-composite life-limited via selective ultrasound application thereto, and the stimulation electrode connected to the triboelectric generator, wherein the stimulation electrode is connected to a nerve to be stimulated so that nerve stimulation treatment is conducted using the current generated from the triboelectric generator.

As shown in FIG. 3, when performing the nerve stimulation treatment, the general ultrasound is applied to the generator to generate the triboelectricity and thus the nerve stimulation electrode may stimulate the nerves using the triboelectricity. When the purpose of the treatment is completed, the focused ultrasound may be applied thereto for decomposition to induce the life-limited nanocomposite material to be decomposed and removed. That is, the device may have a power source that is harmless to the human body and may perform the nerve stimulation treatment using this power source, and then may cause biodegradation at a desired timing after the treatment is completed.

The stimulation electrode my act as a nerve stimulation electrode and may have a structure in which the aforementioned biodegradable conductor (such as magnesium, silicon, PEDOT-PSS, etc.) is encapsulated with an encapsulation portion. Both ends of the stimulation electrode may be respectively connected to the electrode of the triboelectric generator and the nerve to be stimulated. The neurostimulation electrode may be composed of a conductor pattern including several electrodes depending on purposes. That is, the stimulation electrode may be composed of a conductor pattern including one or more electrodes.

To achieve the purpose of the present disclosure, the life-limited nano-composite was manufactured by embedding the nano-carrier decomposed by the application of the focused ultrasound thereto into the life-limited material. The life-limited nano-composite was used to fabricate the neurostimulation device. A treatment effect of peripheral neuropathy using this neurostimulation device was identified via a preclinical test on an animal model of disease/neuropathy.

Although the embodiments of the present disclosure have been described in more detail with reference to the accompanying drawings, the present disclosure is not necessarily limited to these embodiments. The present disclosure may be implemented in various modified manners within the scope not departing from the technical idea of the present disclosure. Accordingly, the embodiments disclosed in the present disclosure are not intended to limit the technical idea of the present disclosure, but to describe the present disclosure. the scope of the technical idea of the present disclosure is not limited by the embodiments. Therefore, it should be understood that the embodiments as described above are illustrative and non-limiting in all respects. The scope of protection of the present disclosure should be interpreted by the claims, and all technical ideas within the scope of the present disclosure should be interpreted as being included in the scope of the present disclosure.

What is claimed is:

1. A triboelectric generator including a nano-composite time-limited via selective ultrasound application thereto, the generator comprising:
   an electrode made of a biodegradable material;
   a membrane disposed to face toward the electrode and spaced apart from the electrode; and
   an encapsulation portion surrounding the electrode and the membrane,
   wherein each of the membrane and the encapsulation portion is made of a nano-composite time-limited via selective ultrasound application thereto,
   wherein the nano-composite includes:
   a life-limited matrix; and
   a nano-carrier embedded or contained in the matrix, wherein the nano-carrier is decomposed when a focused ultrasound is applied thereto,
   wherein when general ultrasound is applied to the nano-composite, the membrane vibrates such that triboelectricity is generated via friction between the membrane and the electrode,
   wherein when the focused ultrasound is applied to the nano-composite, the nano-carrier is decomposed and, thus, the matrix becomes porous, thereby increasing a biodegradation rate of the matrix.

2. The generator of claim 1, wherein the matrix is made of a biodegradable resin.

3. The generator of claim 2, wherein the biodegradable resin includes at least one selected from a group consisting of PLGA (polylactic-co-glycolic acid), PLA (Polylactic Acid), PEG (Polyethylene glycol), PEO (polyethylene oxide), PCL (poly ε-caprolactone), PEEK (Polyetheretherketone), PTHPMA (poly(tetrahydropyranyl-2-methyl methacrylate)), and PPG (Polypropylene Glycol).

4. The generator of claim 1, wherein the nano-carrier includes at least one selected from a group consisting of polymersome, MOF (metal-organic framework), exosome, liposome, ectosome, and nanoparticles.

5. The generator of claim 4, wherein the polymersome includes a block copolymer composed of a life-limited polymer block.

6. The generator of claim 4, wherein the MOF includes a biocompatible ultrasound responsive MOF.

7. The generator of claim 1, wherein the nano-carrier further includes an enzyme or catalyst for promoting the biodegradation rate of the matrix.

8. The generator of claim 1, wherein a dielectric material is coated on a face of the electrode facing toward the membrane to increase the generation of triboelectricity.

9. The generator of claim 1, wherein the electrode, the membrane, and the encapsulation portion constitute one unit of the generator,
   wherein the generator includes a stack of a plurality of units.

* * * * *